United States Patent [19]

Renbarger et al.

[11] 4,107,205
[45] Aug. 15, 1978

[54] α-ARYL-α,α-BIS[ω-(DISUBSTITUTED AMINO)ALKYL]ACETAMIDES AND RELATED COMPOUNDS

[75] Inventors: Jerry J. Renbarger, Arlington Heights; Peter K. Yonan, Morton Grove, both of Ill.

[73] Assignee: G. D. Searle & Co., Chicago, Ill.

[21] Appl. No.: 776,563

[22] Filed: Mar. 11, 1977

[51] Int. Cl.² ............... A61K 31/165; C07C 103/28
[52] U.S. Cl. .................... 260/558 A; 260/239 BF; 260/295 AM; 260/293.69; 260/293.76; 260/326.43; 424/244; 424/248.54; 424/263; 424/267; 424/274; 424/324; 544/131; 544/168; 544/163; 544/124
[58] Field of Search ............. 260/558 A; 424/324

[56] References Cited

U.S. PATENT DOCUMENTS

| 2,884,436 | 4/1959 | Janssen et al. | 260/558 A X |
| 2,894,955 | 7/1959 | Aspergren et al. | 260/558 A X |
| 3,022,314 | 2/1962 | Aspergren et al. | 260/588 A X |
| 3,078,275 | 2/1963 | Moffett et al. | 260/588 A X |
| 3,225,091 | 12/1965 | Ainsworth et al. | 260/558 A |
| 3,344,146 | 9/1967 | Casadio | 260/558 A X |

FOREIGN PATENT DOCUMENTS 673,495  1/1966  Belgium.

OTHER PUBLICATIONS

Casadio et al., *J. Med. Chem.* 8 (5), 594–598 (1965).

*Primary Examiner*—Daniel E. Wyman
*Assistant Examiner*—Thomas A. Waltz
*Attorney, Agent, or Firm*—Dragan J. Karadzic

[57] ABSTRACT

Novel α-aryl-α,α-bis[ω-(disubstituted amino)alkyl]acetamides are described herein. The compounds are useful as anti-arrhythmic agents. The compounds are prepared by reacting an appropriate disubstituted acetonitrile with an appropriate haloalkyl amine and subsequently hydrolyzing the resulting nitrile with concentrated sulfuric acid.

8 Claims, No Drawings

α-ARYL-α,α-BIS[ω-(DISUBSTITUTED AMINO)ALKYL]ACETAMIDES AND RELATED COMPOUNDS

The present invention relates to α-aryl-α,α-bis[ω-(disubstituted amino)alkyl]acetamides having the following general formula

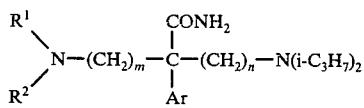

wherein $R^1$ is lower alkyl having from 1 to 7 carbon atoms or cycloalkyl having 5 or 6 carbon atoms; $R^2$ is lower alkyl having from 1 to 7 carbon atoms; or $R^1$ and $R^2$ together with N-atom represents an azamonocyclic ring which may contain further heteroatom; Ar is pyridyl, phenyl, trifluoromethylphenyl or phenyl substituted with 1 or 2 halogen or lower alkyl having from 1 to 4 carbon atoms; and m and n are each integers from 2 to 4 inclusive.

The lower alkyls comprehended by $R^1$ and $R^2$ are methyl, ethyl, propyl, butyl, pentyl, hexyl, heptyl and the branched-chain isomers thereof.

The cycloalkyls comprehended by $R^1$ are cyclopentyl and cyclohexyl.

The halogens comprehended as substituents in the phenyl are fluorine, chlorine, bromine and iodine with fluorine and chlorine being preferred.

The alkyls of 1 to 4 carbon atoms comprehended as substituents in the phenyl are methyl, ethyl, propyl, butyl, and the branched-chain isomers thereof with methyl being preferred.

Positioning of these substituents relative to the point of attachment of the phenyl or, where two are present, to each other is not critical. Thus, within the scope of this invention are o-, m-, or p-monosubstituted phenyls of the type described above, such as o-fluorophenyl, m-chlorophenyl, p-fluorophenyl, p-tolyl and m-trifluoromethylphenyl; and 2,3-, 2,4-, 2,5-, 2,6-, 3,4-, and 3,5-disubstituted phenyls of the type described above, such as 2,4-dichlorophenyl, 2,6-dichlorophenyl, 2,3-difluorophenyl, 3,4-dichlorophenyl, 3-chloro-5-fluorophenyl and 2-fluoro-5-methylphenyl.

The azamonocyclic rings contemplated in the above formula contain from 4 to 6 carbon atoms and are exemplified by piperidino, pyrrolidino, 1H-hexahydroazepin-1-yl, and morpholino.

Equivalent to the foregoing bases for the purposes of this invention are non-toxic pharmacologically acceptable acid addition salts thereof having the formula

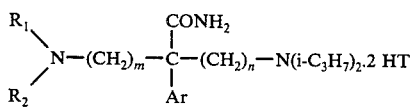

wherein $R^1$, $R^2$, Ar, m and n are as previously defined; and T represents 1 equivalent of an anion — for example, fluoride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, ascorbate, benzoate, cinnamate or the like — which, in combination with the cationic portion of a salt aforesaid, is neither biologically nor otherwise incompatible.

Embodiments of the present invention of the formula

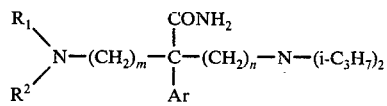

wherein Ar, m and n are as previously defined; $R^1$ is lower alkyl having from 1 to 7 carbon atoms or cycloalkyl having 5 or 6 carbon atoms; and $R^2$ is lower alkyl having from 1 to 7 carbon atoms are preferred embodiments and of these embodiments compounds in which Ar is pyridyl, tolyl, trifluoromethylphenyl or phenyl substituted with 1 or 2 halogen are further preferred.

Compounds of the formula

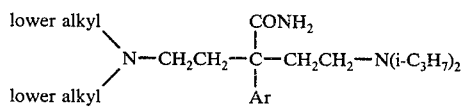

wherein each lower alkyl contains from 1 to 7 carbon atoms and Ar is phenyl substituted with 2 halogen are other preferred embodiments and of these embodiments compounds of the formula

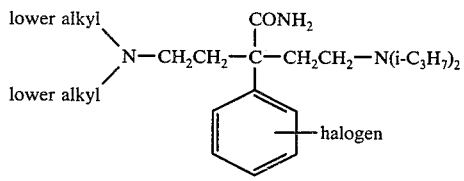

wherein each lower alkyl contains from 1 to 7 carbon atoms are particularly preferred.

Another preferred embodiment of this invention are compounds of the formula

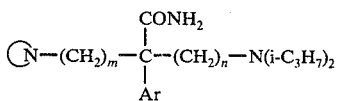

wherein m and n are each integers from 2 to 4 inclusive; Ar is pyridyl, phenyl, tolyl, trifluoromethylphenyl or phenyl substituted with 1 or 2 halogen; and ⟨N⟩- is -N(CH$_2$)$_x$ wherein x is an integer from 4 to 6 inclusive and morpholino, and of these embodiments compounds in which m and n each equal 2 and Ar is phenyl or phenyl substituted with 1 halogen are particularly preferred.

The compounds of this invention are useful because of their pharmacological properties. In particular, they possess activity as anti-arrhythmic agents. Thus, they bring about a return to normal heart rhythm in animals in which the heart rhythm has been irregular.

The anti-arrhythmic activity of the present compounds has been demonstrated in the following way. Ventricular arrhythmia is induced by a 2-stage ligation of the anterior decending branch of the left coronary artery in each of 2 or more dogs. Quantities of test compound (5 mg/kg) are administered intravenously at intervals to a possible maximum accumulated dose of 20 mg/kg. A compound is rated active if it produces at least 25% reduction in ectopic beats for a period of at least 10 minutes in half or more of the dogs tested. Among the compounds of this invention which have been found particularly active in this test are the representative compounds α-(o-fluorophenyl)-α,α-bis[2-(diisopropylamino)ethyl]acetamide, α-(p-fluorophenyl)-α,α-bis[2-(diisopropylamine)ethyl]acetamide and α-(o-chlorophenyl)-α-[2-(diisopropylamino)ethyl]-α-(2-piperidinoethyl)-acetamide.

A further test demonstrating the anti-arrhythmic utility of the present compounds is as follows:

Male mongrel dogs are connected to a physiograph to follow heart and blood action. At the onset of the testing, an initial dose of 40 mcg/kg ouabain is administered intravenously in a saline solution. This is followed 30 minutes later by a dose of 20 mcg/kg of ouabain and, at 15 minute intervals, by a dose of 10 mcg/kg of ouabain until ventricular arrhythmia occurs and persists for 20 minutes. Then, a saline solution of test compound is administered at a dose of 5 mg/kg. If the heart action does not become normal, additional test compound is administered at a dose of 5 mg/kg at 15 minute intervals until heart action becomes normal or until the total dose of test compound administered is 20 mg/kg. The procedure is run in two or more dogs. A compound is considered active if it causes a return to normal heart action for a period of 15 minutes or more in half or more of the dogs tested at a dose of 20 mg/kg or less. Among the compounds of this invention which have been found active in this test are representative compounds α,α-bis[2-(diisopropylamino)ethyl]-α-phenylacetamide and α-[2-(diethylamino)ethyl]-α-[2-(diisopropylamino)ethyl]-α-phenylacetamide.

The compounds of this invention are conveniently prepared by reacting disubstituted acetonitrile of the formula

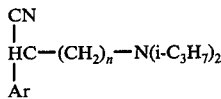

wherein Ar and $n$ are as previously defined with a haloalkyl amine of the formula

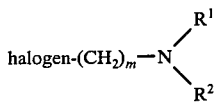

wherein $R^1$, $R^2$ and $m$ are as previously defined and halogen is preferably chlorine, in the presence of a strong base such as sodium amide in an inert solvent such as toluene with heating and subsequently hydrolyzing the resultant nitrile of the formula

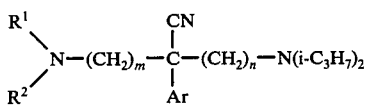

wherein $R^1$, $R^2$, Ar, $m$ and $n$ are as previously defined; with concentrated sulfuric acid.

In an alternate procedure for the preparation of the present compounds in which $R^1$ and $R^2$ are both isopropyl, and $m$ and $n$ are alike integers from 2 to 4, monosubstituted acetonitrile of the formula

wherein Ar is as previously defined, is reacted with two molar equivalents of a haloalkyl amine of the formula

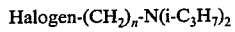

wherein $n$ is as previously defined and halogen is preferably chlorine, in the presence of a strong base such as sodium amide in an inert solvent such as toluene with heating and the resultant nitrile of the formula

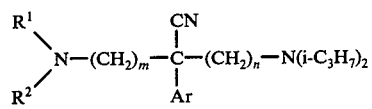

wherein $R^1$, $R^2$, Ar, $m$ and $n$ are as previously defined; is subsequently hydrolyzed with concentrated sulfuric acid.

The invention will appear more fully from the examples which follow. These examples are given by way of illustration only and are not to be construed as limiting the invention either in spirit or in scope as many modifications both in materials and in methods will be apparent from this disclosure to those skilled in the art. In these examples, temperatures are given in degrees Centigrade (° C) and quantities of materials in parts by weight unless parts by volume is specified. The relationship between parts by weight and parts by volume is the same as that existing between grams and milliliters.

EXAMPLE 1

To a solution of 58 parts of α-phenylacetonitrile in 300 parts by volume of toluene is added 83 parts of 2-chloro-N,N-diisopropylethylamine dissolved in 300 parts by volume of toluene. The mixture is heated with stirring to about 80° C and then 22 parts of sodium amide is added slowly over a period of 30 minutes. The mixture is heated at 80° C. for another 30 minutes and then cooled to room temperature. 500 Parts by volume of water is then added to the mixture and the organic layer is separated and extracted with dilute hydrochloric acid. The aqueous acidic extract is made alkaline by the addition of dilute sodium hydroxide. The alkaline mixture is extracted with ether and the ether extract is dried over calcium sulfate, concentrated and distilled to afford α-[2-(diisopropylamino)ethyl]-α-phenylacetonitrile, as an oil boiling at about 120°-125° C. at 0.3 mm pressure. This compound is represented by the following structural formula

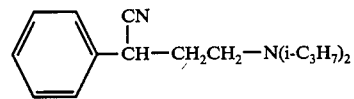

EXAMPLE 2

Method A

The solution of 12 parts of α-phenylacetonitrile and 25 parts of 2-chloro-N,N-diisopropylethylamine in 100 parts by volume of toluene is heated to about 80° C and then 11 parts of sodium amide is added over a period of 30 minutes keeping the temperature at 80°-85° C. The temperature is then raised to about 105° C. and another 25 parts of 2-chloro-N,N-diisopropylethylamine in 100 parts by volume of toluene is added over a period of 20 minutes. The reaction mixture is heated for another hour at 105°-110° C. and then cooled to room temperature when 200 parts by volume of water is added. The organic layer is separated and extracted with dilute hydrochloric acid. The aqueous acidic extract is made alkaline by the addition of dilute sodium hydroxide, extracted with ether and the ether extract dried over calcium sulfate, concentrated and distilled to afford α,α-bis[2-(diisopropylamino)ethyl]-α-phenylacetonitrile, as an oil boiling at about 160°-165° C. at 0.3 mm pressure. This compound is represented by the following structural formula

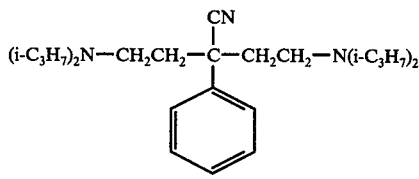

Method B

A solution of 20 parts of α-[2-(diisopropylamino)ethyl]-α-phenylacetonitrile and 4 parts of sodium amide in 180 parts by volume of toluene is heated to about 100° C. over a period of 15 minutes and then 18 parts of 2-chloro-N,N-diisopropylethylamine in 70 parts by volume of toluene is added slowly over a period of 20 minutes. This mixture is heated at 105°-110° C. for an hour and then cooled to room temperature when 200 parts by volume of water is added. The organic layer is separated, dried over calcium sulfate, concentrated and distilled to afford α,α-bis[2-(diisopropylamino)ethyl]-α-phenylacetonitrile as an oil. This compound is identical with the compound of Example 2, Method A.

EXAMPLE 3

2 Parts of α,α-bis[2-(diisopropylamino)ethyl]-α-phenylacetonitrile is dissolved in 20 parts by volume of concentrated sulfuric acid and the resulting solution heated on a steam bath for about 90 minutes. The solution is then cooled to about 0° C. and made alkaline by the addition of dilute sodium hydroxide. The alkaline solution is extracted with ether, the ether extract dried over calcium sulfate and stripped of solvent to afford α,α-bis[2-(diisopropylamino)ethyl]-α-phenylacetamide, melting at about 102°-103° C. after crystallization from hexane. This compound has the following structural formula

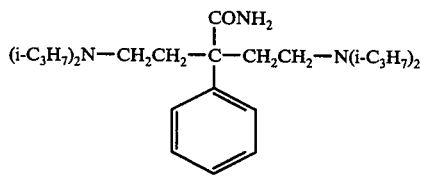

EXAMPLE 4

To a solution of 10 parts of α,α-bis[2-diisopropylamino)ethyl]-α-phenylacetamide in 350 parts by volume of ether is added dropwise with stirring 2 molar equivalents of hydrochloric acid in isopropyl alcohol. The mixture is stirred for about 2 hours when the resulting salt is separated by filtration to afford α,α-bis[2-(diisopropylamino)ethyl]-α-phenylacetamide dihydrochloride, melting at about 140° C.

EXAMPLE 5

Substitution of an equivalent quantity of α-(p-chlorophenyl)acetonitrile for α-phenylacetonitrile called for in Example 2, Method A, affords, by the procedure there detailed, α-(p-chlorophenyl)-α,α-bis[2-(diisopropylamino)ethyl]acetonitrile, as an oil boiling at about 170°-175° C. at 0.3 mm. pressure.

Substitution of an equivalent quantity of the preceding acetonitrile in the procedure of Example 3 affords α-(p-chlorophenyl)-α,α-bis[2-(diisopropylamino)ethyl]acetamide, melting at about 113°-115° C. after crystallication from a mixture of ether and hexane. This compound is represented by the following structural formula

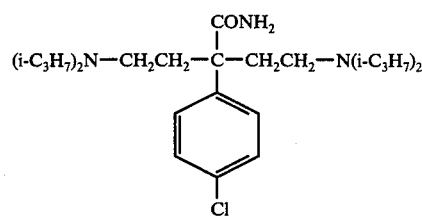

EXAMPLE 6

Substitution of an equivalent quantity of α-(p-fluorophenyl)acetonitrile for α-phenylacetonitrile called for in Example 2, Method A affords, by the procedure there detailed, α-(p-fluorophenyl)-α,α-bis[2-(diisopropylamino)ethyl]acetonitrile, boiling at about 158°-162° C. at 0.3 mm. pressure.

When an equivalent quantity of the preceding acetonitrile is substituted in the procedure of Example 3, there is obtained α-(p-fluorophenyl)-α,α-bis[2-(diisopropylamino)ethyl]acetamide, melting at about 92°-94° C. after crystallization from a mixture of ether and hexane. This compound is represented by the following structural formula

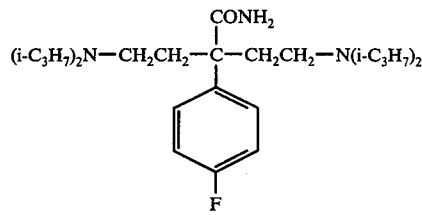

EXAMPLE 7

Substitution of an equivalent quantity of α-(p-tolyl)acetonitrile for α-phenylacetonitrile used in Example 2, Method A and substantial repetition of the procedure detailed in that example, affords α,α-bis[2-(diisopropylamino)ethyl]-α-(p-tolyl)acetonitrile, as an oil boiling at about 160°-163° C. at 0.3 mm pressure.

A mixture of 10 parts of the preceding acetonitrile, 20 parts of potassium hydroxide, 2 parts by volume of water and 50 parts by volume of ethanol is refluxed for 22 hours. The mixture is then cooled to room temperature, poured into water and extracted with ether. The ether extract is dried over calcium sulfate and stripped of solvent to afford an oil which solidifies upon standing. The crude solid is crystallized from pentane to afford α,α-bis[2-(diisopropylamino)ethyl]-α-(p-tolyl- )acetamide, melting at about 97°–100° C. This compound is represented by the following structural formula

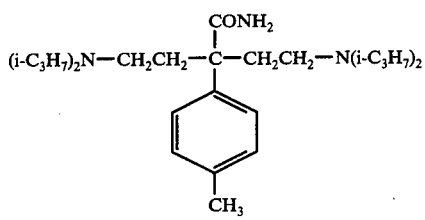

EXAMPLE 8

Substitution of an equivalent quantity of 2-chloro-N,N-dimethylethylamine for 2-chloro-N,N-diisopropylethylamine called for in Example 2, Method B affords by the procedure there detailed, α-[2-(diisopropylamino)ethyl]-α-[2-(dimethylamino)ethyl]-α-phenylacetonitrile, as an oil boiling at about 170°–173° C. at 0.1 mm pressure.

When an equivalent quantity of the preceding acetonitrile is substituted in the procedure of Example 3, there is obtained α-[2-(diisopropylamino)ethyl]-α-[2-(dimethylamino)ethyl]-α-phenylacetamide, melting at about 75°–78° C. after crystallization from pentane. This compound is represented by the following structural formula

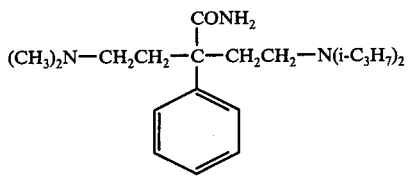

EXAMPLE 9

Substitution of an equivalent quantity of 1-(2-chloroethyl)piperidine for 2-chloro-N,N-diisopropylethylamine called for in Example 2, Method B affords, by the procedure there detailed, α-[2-(diisopropylamino)ethyl]-α-phenyl-α-(2-piperidinoethyl)acetonitrile, as an oil.

When an equivalent quantity of the preceding acetonitrile is substituted in the procedure of Example 3, there is obtained α-[2-(diisopropylamino)ethyl]-α-phenyl-α-(2-piperidinoethyl)acetamide, melting at about 72°–75° C. after crystallization from pentane. This compound is represented by the following structural formula

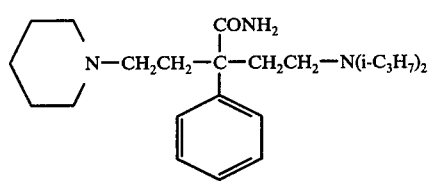

EXAMPLE 10

Substitution of an equivalent quantity of α-(m-chlorophenyl)acetonitrile for α-phenylacetonitrile used in Example 2, Method A and substantial repetition of the procedure detailed in that example, affords α-(m-chlorophenyl)-α,α-bis[2-(diisopropylamino)ethyl]acetonitrile, as an oil boiling at about 165°–175° C. at 0.1 mm pressure.

When an equivalent quantity of the preceding acetonitrile is substituted in the procedure of Example 3, there is obtained α-(m-chlorophenyl)-α,α-bis[2-(diisopropylamino)ethyl]acetamide, melting at about 102°–105° C. after crystallization from a mixture of ether and hexane. This compound is represented by the following structural formula

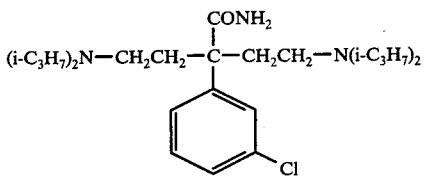

EXAMPLE 11

Substitution of an equivalent quantity of α-(2,4-dichlorophenyl)acetonitrile for α-phenylacetonitrile used in Example 2, Method A and substantial repetition of the procedure detailed in that example, affords α-(2,4-dichlorophenyl)-α,α-bis[2-(diisopropylamino)ethyl]acetonitrile, as an oil boiling at about 175°–185° C. at 0.1 mm pressure.

When an equivalent quantity of the preceding acetonitrile is substituted in the procedure of Example 3, there is obtained α-(2,4-dichlorophenyl)-α,α-bis[2-(diisopropylamino)ethyl]acetamide, melting at about 160°–161° C. after crystallization from a mixture of ether and hexane. This compound is represented by the following structural formula

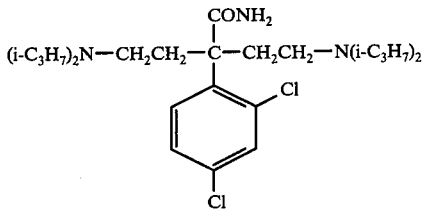

EXAMPLE 12

Substitution of an equivalent quantity of 4-(2-chloroethyl)morpholine for 2-chloro-N,N-diisopropylethylamine called for in Example 2, Method B affords, by the procedure there detailed, α-[2-(diisopropylamino)ethyl]-α-(2-morpholinoethyl)-α-phenylacetonitrile, as an oil.

When an equivalent quantity of the preceding acetonitrile is substituted in the procedure of Example 3, there is obtained α-[2-(diisopropylamino)ethyl]-α-(2-morpholinoethyl)-α-phenylacetamide. This compound melts at about 87°–89° C. after crystallization from a mixture of ether and pentane and is represented by the following structural formula

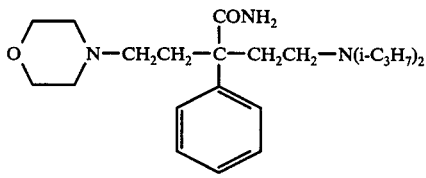

EXAMPLE 13

Substitution of an equivalent quantity of α-(3,4-dichlorophenyl)acetonitrile for α-phenylacetonitrile called for in Example 2, Method A affords, by the procedure there detailed, α-(3,4-dichlorophenyl)α,α-bis[2-(diisopropylamino)ethyl]acetonitrile, as an oil boiling at about 170°–200° C. at 0.2–0.6 mm pressure.

When an equivalent quantity of the preceding acetonitrile is substituted in the procedure of Example 3, there is obtained α-(3,4-dichlorophenyl)-α,α-bis[2-(diisopropylamino)ethyl]acetamide. This compound melts at about 105°–108° C. and is represented by the following structural formula

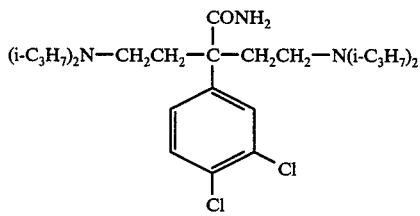

EXAMPLE 14

Substitution of an equivalent quantity of α-(m-fluorophenyl)acetonitrile for α-phenylacetonitrile used in Example 2, Method A and substantial repetition of the procedure detailed in that example affords, α-(m-fluorophenyl)-α,α-bis[2-(diisopropylamino)ethyl]acetonitrile, as an oil boiling at about 160°–163° C. at 0.2 mm. pressure.

Substitution of an equivalent quantity of the preceding acetonitrile in the procedure of Example 3 affords, α-(m-fluorophenyl)-α,α-bis[2-(diisopropylamino)ethyl]acetamide, melting at about 118°–120° C. after crystallization from a mixture of ether and pentane. This compound is represented by the following structural formula

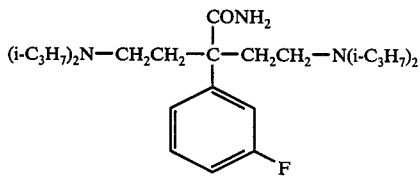

EXAMPLE 15

Substitution of an equivalent quantity of α-(o-fluorophenyl)acetonitrile for α-phenylacetonitrile called for in Example 2, Method A affords, by the procedure there detailed α-(o-fluorophenyl)-α,α-bis[2-(diisopropylamino)ethyl]acetonitrile, as an oil.

When an equivalent quantity of the preceding acetonitrile is substituted in the procedure of Example 3, there is obtained α-(o-fluorophenyl)-α,α-bis[2-(diisopropylamino)ethyl]acetamide, melting at about 121°–123° C. This compound is represented by the following structural formula

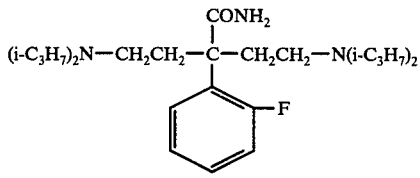

EXAMPLE 16

Substitution of an equivalent quantity of α-(o-trifluoromethylphenyl)acetonitrile for α-phenylacetonitrile called for in Example 2, Method A affords, by the procedure detailed in that example, α-(o-trifluoromethylphenyl)-α,α-bis[2-(diisopropylamino)ethyl]acetonitrile, as an oil boiling at about 155°–160° C. at 0.3 mm pressure.

When an equivalent quantity of the preceding acetonitrile is substituted in the procedure of Example 3, there is obtained α-(o-trifluoromethylphenyl)-α,α-bis[2-(diisopropylamino)ethyl]acetamide, melting at about 131°–132° C. after crystallization from a mixture of ether and hexane. This compound is represented by the following structural formula

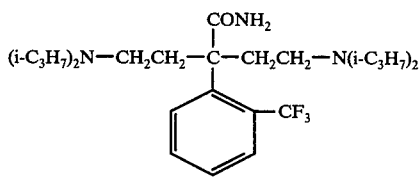

EXAMPLE 17

When an equivalent quantity of α-(p-fluorophenyl)acetonitrile is substituted for α-phenylacetonitrile called for in Example 1 and the procedure detailed in that example is substantially repeated, there is obtained α-(p-fluorophenyl)-α-[2-(diisopropylamino)ethyl]acetonitrile, as an oil boiling at about 125°–130° C. at 0.5 mm. pressure.

Substitution of equivalent quantities of α-(p-fluorophenyl)-α-[2-(diisopropylamino)ethyl]acetonitrile and 2-chloro-N,N-dimethylethylamine for α-[2-(diisopropylamino)ethyl]-α-phenylacetonitrile and 2-chloro-N,N-diisopropylethylamine called for respectively in the procedure of Example 2, Method B, there is obtained α-(p-fluorophenyl)-α-[2-(diisopropylamino)ethyl]-α-[2-(dimethylamino)ethyl]acetonitrile, as an oil.

When an equivalent quantity of the preceding acetonitrile is substituted in the procedure of Example 3, there is obtained α-(p-fluorophenyl)-α-[2-(diisopropylamino)ethyl]-α-[2-(dimethylamino)ethyl]acetamide, melting at about 78°–80° C after crystallization from pentane. This compound is represented by the following structural formula

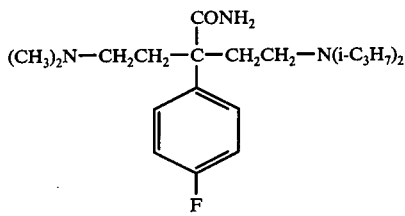

EXAMPLE 18

Substitution of an equivalent quantity of 1-(2-chloroethyl)piperidine for 2-chloro-N,N-dimethylethylamine called for in Example 17 and substantial repetition of the procedure detailed in the second paragraph of that example affords, α-(p-fluorophenyl)-α-[2-(diisopropylamino)ethyl]-α-(2-piperidinoethyl)acetonitrile, as an oil.

When an equivalent quantity of the preceding acetonitrile is substituted in the procedure of Example 3, there is obtained α-(p-fluorophenyl)-α-[2-(diisopropylamino)ethyl]-α-(2-piperidinoethyl)acetamide. This compound melts at about 99°-101° C. and is represented by the following structural formula

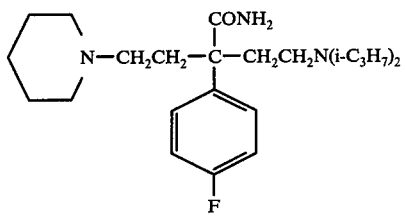

EXAMPLE 19

When an equivalent quantity of α-(o-chlorophenyl)acetonitrile is substituted for α-phenylacetonitrile called for in Example 1 and the procedure detailed in that example substantially repeated, there is obtained α-(o-chlorophenyl)-α-[2-(diisopropylamino)ethyl]acetonitrile as an oil boiling at about 130°-135° C. at 0.5 mm. pressure.

Substitution of an equivalent quantity of the preceding acetonitrile for α-[2-(diisopropylamino)ethyl]-α-phenylacetonitrile called for in Example 2, Method B and substantial repetition of the procedure detailed in that example, affords α-(o-chlorophenyl)-α,α-bis[2-diisopropylamino)ethyl]acetonitrile, as an oil.

Substitution of an equivalent quantity of the preceding acetonitrile in the procedure of Example 3 affords, α-(o-chlorophenyl)-α,α-bis[2-(diisopropylamino)ethyl]acetamide, melting at about 157°-158° C. after crystallization from a mixture of ether and hexane. This compound is represented by the following structural formula

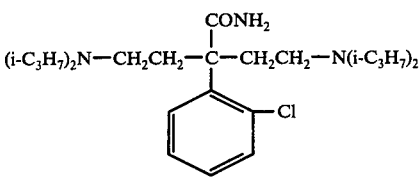

EXAMPLE 20

When an equivalent quantity of α-(o-fluorophenyl)acetonitrile is substituted for α-phenylacetonitrile called for in Example 1 and the procedure detailed in that example substantially repeated, there is obtained α-(o-fluorophenyl)-α-[2-(diisopropylamino)ethyl]acetonitrile, as an oil boiling at about 120°-125° C. at 0.5 mm. pressure.

Substitution of equivalent quantities of α-(o-fluorophenyl)-α-[2-(diisopropylamino)ethyl]acetonitrile and 1-(2-chloroethyl)piperidine for α-[2-(diisopropylamino)ethyl]-α-phenylacetonitrile and 2-chloro-N,N-diisopropylethylamine called for respectively in the procedure of Example 2, Method B affords, α-(o-fluorophenyl)-α-[2-(diisopropylamino)ethyl]-α-(2-piperidinoethyl)acetonitrile, as an oil boiling at about 168°-172° C. at 0.3 mm. pressure.

When an equivalent quantity of the preceding acetonitrile is substituted in the procedure of Example 3, there is obtained α-(o-fluorophenyl)-α-[2-(diisopropylamino)ethyl]-α-(2-piperidinoethyl)acetamide, melting at about 107°-108° C. after crystallization from a mixture of ether and hexane. This compound is represented by the following structural formula

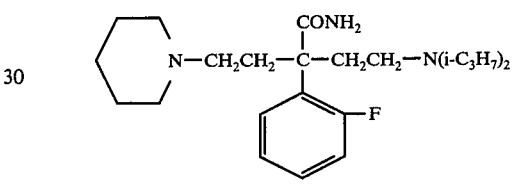

EXAMPLE 21

When an equivalent quantity of α-(o-chlorophenyl)-α-[2-(diisopropylamino)ethyl]acetonitrile prepared according to the first paragraph of Example 19, is substituted for α-(o-fluorophenyl)-α-[2-(diisopropylamino)ethyl]acetonitrile called for in Example 20 and the procedure detailed in the second paragraph of that example is substantially repeated, there is obtained α-(o-chlorophenyl)-α-[2-(diisopropylamino)ethyl]-α-(2-piperidinoethyl)acetonitrile, as an oil boiling at about 190°-195° C. at 0.3 mm. pressure.

Substitution of an equivalent quantity of the preceding acetonitrile in the procedure of Example 3 affords, α-(o-chlorophenyl)-α-[2-(diisopropylamino)ethyl]-α-(2-piperidinoethyl)acetamide. This compound melts at about 130°-131° C. after crystallization from a mixture of ether and hexane and is represented by the following structural formula

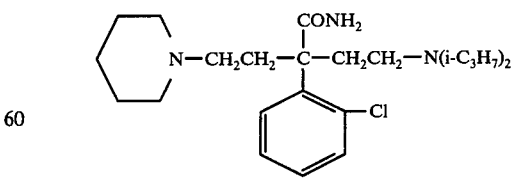

EXAMPLE 22

Substitution of equivalent quantities of α-(o-chlorophenyl)-α-[2-(diisopropylamino)ethyl]acetonitrile and 2-chloro-N,N-dimethylethylamine for α-[2-(diisopropylamino)ethyl]-α-phenylacetonitrile and 2-chloro-N,N-diisopropylethylamine called for respectively in the procedure of Example 2, Method B, there is obtained α-(o-chlorophenyl)-α-[2-(diisopropylamino)ethyl]-α-[2-(dimethylamino)ethyl]acetonitrile, as an oil boiling at about 160°-165° C. at 0.5 mm. pressure.

When an equivalent quantity of the preceding acetonitrile is substituted in the procedure of Example 3, there is obtained α-(o-chlorophenyl)-α-[2-(diisopropylamino)ethyl]-α-[2-(dimethylamino)ethyl]acetamide, melting at about 111°-112° C. after crystallization from a mixture of ether and hexane. This compound is represented by the following structural formula

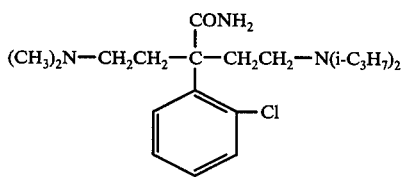

EXAMPLE 23

When an equivalent quantity of α-(2,6-dichlorophenyl)acetonitrile is substituted for α-phenylacetonitrile called for in Example 1 and the procedure detailed in that example substantially repeated, there is obtained α-(2,6-dichlorophenyl)-α-[2-(diisopropylamino)ethyl]acetonitrile, as an oil boiling at about 160°-163° C. at 0.5mm. pressure.

Substitution of the preceding acetonitrile for α-[2-(diisopropylamino)ethyl]-α-phenylacetonitrile called for in Example 2, Method B and substantial repetition of the procedure detailed in that example, affords α-(2,6-dichlorophenyl)-α,α-bis[2-(diisopropylamino)ethyl]acetonitrile, as an oil boiling at about 180°-185° C. at 0.3 mm. pressure.

When an equivalent quantity of the preceding acetonitrile is substituted in the procedure of Example 3, there is obtained α-(2,6-dichlorophenyl)-α,α-bis[2-(diisopropylamino)ethyl]acetamide, melting at about 168°-170° C. after crystallization from a mixture of methylene chloride and hexane. This compound is represented by the following structural formula

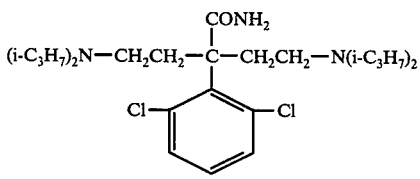

EXAMPLE 24

Substitution of equivalent quantities of α-(o-fluorophenyl)-α-[2-(diisopropylamino)ethyl]acetonitrile and 2-chloro-N-cyclohexyl-N-methylethylamine for α-[2-(diisopropylamino)ethyl]-α-phenylacetonitrile and 2-chloro-N,N-diisopropylethylamine called for respectively in the procedure of Example 2, Method B, affords α-(o-fluorophenyl)-α-[2-(diisopropylamino)ethyl]-α-{2-[N-cyclohexyl(methylamino)]ethyl}acetonitrile, as an oil boiling at about 185°-190° C. at 0.3 mm. pressure.

When an equivalent quantity of the preceding acetonitrile is substituted in the procedure of Example 3, there is obtained α-(o-fluorophenyl)-α-[2-(diisopropylamino)ethyl]-α-{2-[N-cyclohexyl(methylamino)]ethyl}acetamide. This compound melts at about 114°-115° C. after crystallization from a mixture of methylene chloride and hexane and is represented by the following structural formula

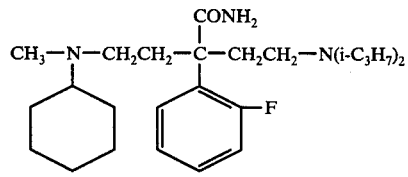

EXAMPLE 25

Substitution of an equivalent quantity of 3-chloro-N,N-diisopropylpropylamine for 2-chloro-N,N-diisopropylethylamine called for in Example 2, Method B and substantial repetition of the procedure detailed in that example affords, α-[2-(diisopropylamino)ethyl]-α-[3-(diisopropylamino)propyl]-α-phenylacetonitrile.

When an equivalent quantity of the preceding acetanitrile is substituted in the procedure of Example 3, there is obtained α-[2-(diisopropylamino)ethyl]-α-[3-(diisopropylamino)propyl]-α-phenylacetamide. This compound is represented by the following structural formula

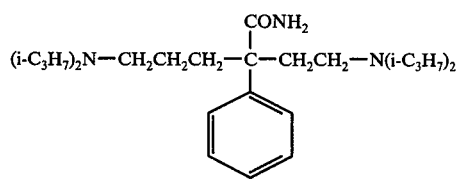

EXAMPLE 26

A mixture of 6 parts of α,α-bis[2-(diisopropylamino)ethyl]-α-phenylacetamide, 20 parts by volume of methyl iodide and 150 parts by volume of acetone is placed in a bomb and heated at 65° C. for about 3 hours. To the solidified reaction mixture is then added more acetone and the solid is filtered off and crystallized from a mixture of ethyl alcohol and ether. The compound thus obtained is α,α-bis[2-(diisopropylamino)ethyl]-α-phenylacetamide bismethiodide, melting at about 213°-214° C. This compound is represented by the following structural formula

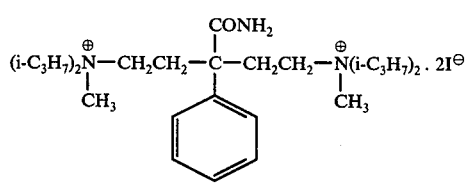

EXAMPLE 27

Substitution of an equivalent quantity of 2-chloro-N,N-diethylethylamine for 2-chloro-N,N-diisopropylethylamine called for in Example 2, Method B and substantial repetition of the procedure detailed in that example affords α-[2-(diethylamino)ethyl]-α-[2-(diisopropylamino)ethyl]-α-phenylacetonitrile, as an oil boiling at about 147°-150° C. at 0.2 mm. pressure.

When an equivalent quantity of the preceding acetonitrile is substituted in the procedure of Example 3, there is obtained α-[2-(diethylamino)ethyl]-α-[2-(diisopropylamino)ethyl]-α-phenylacetamide, melting at about 90°–91° C. This compound is represented by the following structural formula

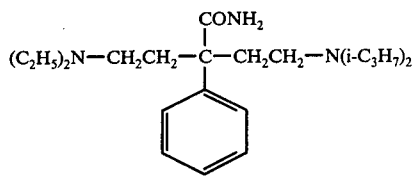

EXAMPLE 28

Substitution of an equivalent quantity of 1-(3-chloropropyl)piperidine for 2-chloro-N,N-diisopropylethylamine called for in the procedure of Example 2, Method B affords, by the procedure there detailed α-[2-(diisopropylamino)ethyl]-α-phenyl-α-(3-piperidinopropyl)acetonitrile.

When an equivalent quantity of the preceding acetonitrile is substituted in the procedure of Example 3, there is obtained α-[2-(diisopropylamino)ethyl]-α-phenyl-α-(3-piperidinopropyl)acetamide. This compound is represented by the following structural formula

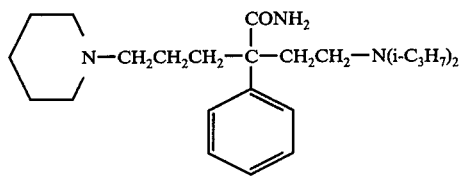

EXAMPLE 29

When an equivalent quantity of α-(2-pyridyl)acetonitrile is substituted for α-phenylacetonitrile called for in Example 1 and the procedure detailed in that example substantially repeated, there is obtained α-[2-(diisopropylamino)ethyl]-α-(2-pyridyl)acetonitrile, as an oil boiling at about 125°–130° C. at 0.3 mm. pressure.

Substitution of an equivalent quantity of the preceding acetonitrile for α-[2-(diisopropylamino)ethyl]-α-phenylacetonitrile called for in Example 2, Method B and substantial repetition of the procedure detailed in that example, affords α,α-bis[2-(diisopropylamino)ethyl]-α-(2-pyridyl)acetonitrile, as an oil boiling at about 155°–160° C. at 0.3 mm. pressure.

When an equivalent quantity of the preceding acetonitrile is substituted in the procedure of Example 3, there is obtained α,α-bis[2-(diisopropylamino)ethyl]-α-(2-pyridyl)acetamide, melting at about 156°–157° C. after crystallization from a mixture of methylene chloride and hexane. This compound is represented by the following structural formula

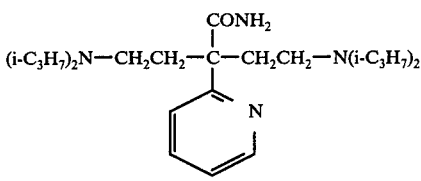

EXAMPLE 30

Substitution of an equivalent quantity of 3-chloro-N,N-dimethylpropylamine for 2-chloro-N,N-diisopropylethylamine called for in Example 2, Method B affords, by the procedure there detailed, α-[2-(diisopropylamino)ethyl]-α-[3-(dimethylamino)propyl]-α-phenylacetonitrile.

Substitution of the preceding acetonitrile in the procedure of Example 3 affords, α-[2-(diisopropylamino)ethyl]-α-[3-(dimethylamino)propyl]-α-phenylacetamide.

EXAMPLE 31

Substitution of equivalent quantities of α-(o-fluorophenyl)-α-[2-(diisopropylamino)ethyl]acetonitrile and 1-(2-chloroethyl)pyrrolidine for α-[2-(diisopropylamino)ethyl]-α-phenylacetonitrile and 2-chloro-N,N-diisopropylethylamine called for respectively in the procedure of Example 2, Method B affords, α-(o-fluorophenyl)-α-[2-(diisopropylamino)ethyl]-α-(2-pyrrolidinoethyl)acetonitrile, as an oil boiling at about 155°–160° C. at 0.1 mm. pressure.

When an equivalent quantity of the preceding acetonitrile is substituted in the procedure of Example 3, there is obtained α-(o-fluorophenyl)-α-[2-(diisopropylamino)ethyl]-α-(2-pyrrolidinoethyl)acetamide, melting at about 104°–105° C. after crystallization from a mixture of ether and hexane. This compound is represented by the following structural formula

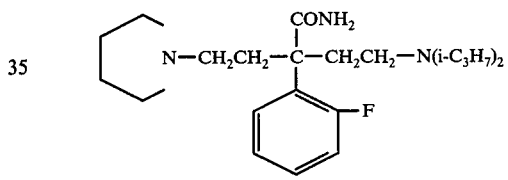

EXAMPLE 32

Substitution of equivalent quantities of α-[2-(diisopropylamino)ethyl]-α-(2-pyridyl)acetonitrile and 1-(2-chloroethyl)piperidine for α-[2-(diisopropylamino)ethyl]-α-phenylacetonitrile and 2-chloro-N,N-diisopropylethylamine called for respectively in the procedure of Example 2, Method B affords α-[2-(diisopropylamino)ethyl]-α-(2-piperidinoethyl)-α-(2-pyridyl)acetonitrile, as an oil boiling at about 160°–170° C. at 0.5–0.7 mm. pressure.

Substitution of the preceding acetonitrile in the procedure of Example 3 affords, α-[2-(diisopropylamino)ethyl]-α-(2-piperidinoethyl)-α-(2-pyridyl)acetamide melting at about 129°–131° C. after crystallization from a mixture of methylene chloride and hexane. This compound is represented by the following structural formula

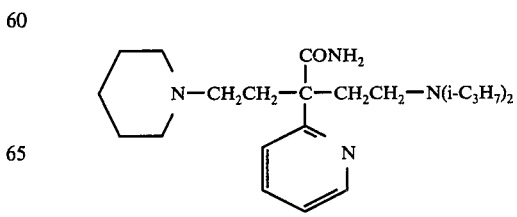

EXAMPLE 33

Substitution of an equivalent quantity of 1-(2-chloroethyl)-1H-hexahydroazepine for 2-chloro-N,N-diisopropylethylamine called for in Example 2, Method B affords, by the procedure there detailed, α-[2-(1H-hexahydroazepin-1-yl)ethyl]-α-[2-(diisopropylamino)ethyl]-α-phenylacetonitrile, as an oil boiling at about 160°–165° C. at 0.1 mm. pressure.

Substitution of the preceding acetonitrile in the procedure of Example 3 affords α-[2-(1H-hexahydroazepin-1-yl)ethyl]-α-[2-(diisopropylamino)ethyl]-α-phenylacetamide. This compound melts at about 58°–60° C. after crystallization from pentane and is represented by the following structural formula

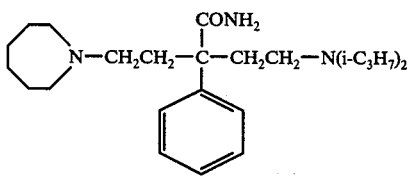

EXAMPLE 34

Substitution of equivalent quantities of α-(o-fluorophenyl)-α-[2-(diisopropylamino)ethyl]acetonitrile and 1-(2-chloroethyl)-1H-hexahydroazepine for α-[2-(diisopropylamino)ethyl]-α-phenylacetonitrile and 2-chloro-N,N-diisopropylethylamine called for respectively in the procedure of Example 2, Method B affords α-(o-fluorophenyl)-α-[2-(1H-hexahydroazepin-1-yl)ethyl]-α-[2-(diisopropylamino)ethyl]acetonitrile, as an oil boiling at about 170°–175° C. at 0.3 mm. pressure.

Substitution of the preceding acetonitrile in the procedure of Example 3 affords α-(o-fluorophenyl)-α-[2-(1H-hexahydroazepin-1-yl)ethyl]-α-[2-(diisopropylamino)ethyl]acetamide, melting at about 108°–109° C after crystallization from pentane.

EXAMPLE 35

Substitution of an equivalent quantity of 1-(2-chloroethyl)pyrrolidine for 2-chloro-N,N-diisopropylethylamine called for in Example 2, Method B affords, by the procedure there detailed, α-[2-(diisopropylamino)ethyl]-α-phenyl-α-(2-pyrrolidinoethyl)acetonitrile, as an oil boiling at about 150°–155° C. at 0.2 mm. pressure.

Substitution of the preceding acetonitrile in the procedure of Example 3 affords α-[2-(diisopropylamino)ethyl]-α-phenyl-α-(2-pyrrolidinoethyl)acetamide, melting at about 79°–80° C.

EXAMPLE 36

Substitution of an equivalent quantity of 2-chloro-N-cyclohexyl-N-methylethylamine for 2-chloro-N,N-diisopropylethylamine called for in Example 2, Method B affords, by the procedure there detailed, α-[2-(diisopropylamino)ethyl]-α-{2-[N-cyclohexyl(methylamino)]ethyl}-α-phenylacetonitrile, as an oil boiling at about 185°–190° C. at 0.5 mm. pressure.

Substitution of the preceding acetonitrile in the procedure of Example 3 affords α-[2-(diisopropylamino)ethyl]-α-{2-[N-cyclohexyl(methylamino)]ethyl}-α-phenylacetamide, melting at about 90°–91° C. This compound is represented by the following structural formula

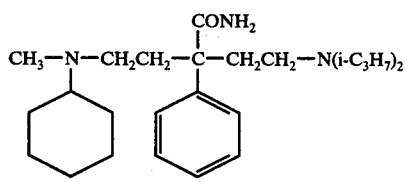

EXAMPLE 37

Substitution of an equivalent quantity of 2-chloro-N-ethyl-N-methylethylamine for 2-chloro-N,N-diisopropylethylamine called for in Example 2, Method B, affords, by the procedure there detailed, α-[2-(ethylmethylamino)ethyl]-α-[2-(diisopropylamino)ethyl]-α-phenylacetonitrile.

Substitution of the preceding acetonitrile in the procedure of Example 3 affords α-[2-(ethylmethylamino)ethyl]-α-[2-(diisopropylamino)ethyl]-α-phenylacetamide. This compound is represented by the following structural formula

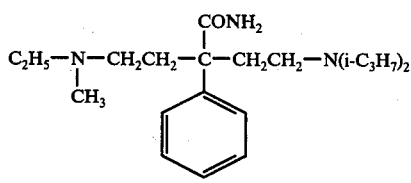

What we claim is:
1. A compound of the formula

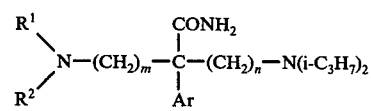

and the non-toxic pharmacologically acceptable acid addition salts thereof; wherein $R^1$ is lower alkyl having from 1 to 7 carbon atoms or cycloalkyl having 5 or 6 carbon atoms; $R^2$ is lower alkyl having from 1 to 7 carbon atoms; Ar is phenyl, trifluoromethylphenyl or phenyl substituted with 1 or 2 halogen or lower alkyl having from 1 to 4 carbon atoms; and $m$ and $n$ are each integers from 2 to 4 inclusive.

2. A compound according to claim 1 having the formula

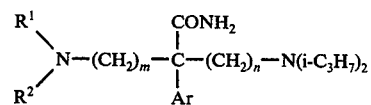

and the non-toxic pharmacologically acceptable acid addition salts thereof; wherein $R^1$ is lower alkyl having from 1 to 7 carbon atoms or cycloalkyl having 5 or 6 carbon atoms; $R^2$ is lower alkyl having from 1 to 7 carbon atoms; Ar is tolyl, trifluoromethylphenyl or phenyl substituted with 1 or 2 halogen; and $m$ and $n$ are each integers from 2 to 4 inclusive.

3. A compound according to claim 1 having the formula

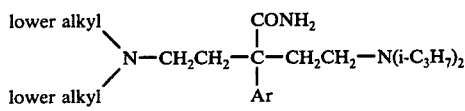

and the non-toxic pharmacologically acceptable acid addition salts thereof; wherein each lower alkyl contains from 1 to 7 carbon atoms; and Ar is phenyl substituted with 2 halogens.

4. A compound according to claim 1 having the formula

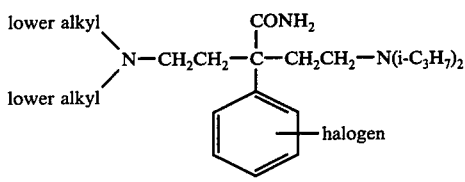

and the non-toxic pharmacologically acceptable acid addition salts thereof; wherein each lower alkyl contains from 1 to 7 carbon atoms.

5. A compound according to claim 1 having the formula

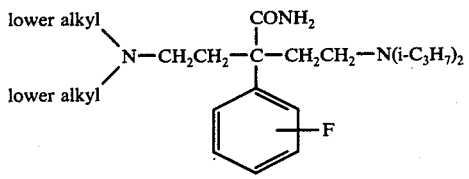

and the non-toxic pharmacologically acceptable acid addition salts thereof; wherein each lower alkyl contains from 1 to 7 carbon atoms.

6. A compound according to claim 1 having the formula

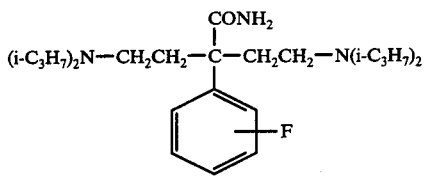

and the non-toxic pharmacologically acceptable acid addition salts thereof.

7. A compound according to claim 1 which is α-(p-fluorophenyl)-α,α-bis[2-(diisopropylamino)ethyl]acetamide.

8. A compound according to claim 1 which is α-(o-fluorophenyl)-α,α-bis[2-(diisopropylamino)ethyl]acetamide.

* * * * *